United States Patent [19]

Tehrani

[11] Patent Number: 4,986,268

[45] Date of Patent: Jan. 22, 1991

[54] METHOD AND APPARATUS FOR CONTROLLING AN ARTIFICIAL RESPIRATOR

[76] Inventor: Fleur T. Tehrani, 2601 Pennsylvania Ave., Apt. 947, Philadelphia, Pa. 19130

[21] Appl. No.: 233,455

[22] Filed: Aug. 18, 1988

Related U.S. Application Data

[63] Continuation-in-part of Ser. No. 178,019, Apr. 6, 1988, abandoned.

[51] Int. Cl.[5] .......... A61M 16/00

[52] U.S. Cl. .......... 128/204.22

[58] Field of Search .......... 128/204.21, 204.22, 128/204.23, 718, 720, 736

[56] References Cited

U.S. PATENT DOCUMENTS

| | | | |
|---|---|---|---|
| 3,621,833 | 11/1971 | Crane | 128/720 |
| 4,036,221 | 7/1977 | Hillsman et al. | 128/204.23 |
| 4,192,001 | 3/1980 | Villa | 128/204.23 |
| 4,265,237 | 5/1981 | Schwanbom et al. | 228/204.24 |
| 4,326,513 | 4/1982 | Schulz et al. | 128/204.23 |
| 4,333,476 | 6/1982 | Downing, Jr. | 128/720 |
| 4,336,590 | 6/1982 | Jacq et al. | 364/418 |
| 4,351,344 | 9/1982 | Stenzler | 128/720 |
| 4,380,233 | 4/1983 | Caillot | 128/204.21 |
| 4,386,604 | 6/1983 | Hershey | 128/736 |
| 4,450,527 | 5/1984 | Sramek | 128/720 |
| 4,471,773 | 9/1984 | Bunnell et al. | 128/204.21 |
| 4,537,190 | 8/1985 | Caillot et al. | 128/204.22 |
| 4,567,888 | 2/1986 | Robert et al. | 128/204.21 |
| 4,617,924 | 10/1986 | Heim et al. | 128/204.23 |
| 4,619,269 | 10/1986 | Cutler et al. | 128/718 |
| 4,627,860 | 12/1986 | Rowland | 55/162 |
| 4,635,631 | 1/1987 | Izumi | 128/204.23 |
| 4,651,729 | 3/1987 | Rae | 128/204.22 |
| 4,665,911 | 5/1987 | Williams et al. | 128/204.21 |
| 4,671,297 | 6/1987 | Schulze, Jr. | 128/204.23 |

FOREIGN PATENT DOCUMENTS 0046570 3/1982 European Pat. Off. .

OTHER PUBLICATIONS

"An Algorithm For Automatic Control of $O_2$ and $CO_2$ in Artificial Ventilation", Marie Helene Giard, Francois Olivier Berstrand, Dominique Robert, and Jacques Pernier, *IEEE Transactions on Biomedical Engineering,* vol. BME-32, No. 9, Sep. 1985.

"A Feedback Controller for Ventilatory Therapy", F. W. Chapman, J. C. Newell and R. J. Roy, *Anals of Biomedical Engineering,* vol. 13, pp. 359–372, 1985.

"Improvement in Arterial Oxygen Control Using Multiple-Model Adaptive Control Procedures", Clement Yu, W. G. He, James M. So, Rob Roy, Howard Kaufman and Jonathan C. Newell, *IEEE Transactions on Biomedical Engineering,* vol. BME-34, No. 8, Aug. 1987.

"Operating Room Care With Microprocessor Based Closed-Loop Controllers", D. R. Westenskow, Ph.D., Department of Anesthesiology, Uni. of Utah, Salt Lake (List continued on next page.)

*Primary Examiner*—Edgar S. Burr
*Assistant Examiner*—Aaron J. Lewis
*Attorney, Agent, or Firm*—Woodcock, Washburn, Kurtz, Mackiewicz & Norris

[57] ABSTRACT

An apparatus for automatically controlling an artificial respirator includes sensors for receiving the exhaust gas from a patient and providing data signals corresponding to the concentration of the carbon dioxide and oxygen in the gas. The data signals are provided to a microcomputer which, together with data representing at least the patient's lung elastance factor, air viscosity factor in the lungs and barometric pressure, and when the patient is in exercise, metabolic rate ratio, determines the total ventilation and frequency for the patient's next breath and provides data output signals corresponding thereto. The data output signals from the microcomputer are provided, in analog form, to a signal generator and timing control circuit. This circuit provides output pulses which control the respirator and control valves between the respirator and the sensors.

27 Claims, 8 Drawing Sheets

OTHER PUBLICATIONS

City, *IEEE Transactions on Biomedical Engineering*, vol. BME-29, No. 8, Aug. 1982.

"Computer Control of Respiration and Anesthesia", J. R. Coles, W. A. Brown, D. G. Lampard, Dept. of Electrical Engineering, Monash University, *Medical and Biological Engineering*-May, 1973.

"A Mathematical Model of the Human Respiratory System", W. F. Fincham and F. T. Tehrani, *Journal of Biomedical Engineering*, Apr., 1983.

"A Dynamic Model of the Respiratory System", W. F. Fincham and F. T. Tehrani, *Strathclyde Bioengineering Seminar Series*, Aug., 1981.

"On the Regulation of Cardiac Output and Cerebral Blood Flow", W. F. Fincham and F. T. Tehrani, *Journal of Biomedical Engineering*, vol. 5, pp. 74–75, Jan. 1983.

"A Dual Control System For Assisting Respiration", Y. Mitamura, T. Mikami, K. Yamamoto and K. Mimura, *Medical & Biological Engineering*, vol. 13, No. 6, pp. 846–854, Nov. 1975.

"An Optimally Controlled Respirator", Yoshinori Mitamura, Tomohisa Mikami, Hiromi Sugawara and Chiyoshi Yoshimoto, *IEEE Transactions on Biomedical Engineering*, BME-18, pp. 330-337, 1971.

"A Microprocessor14 Controlled Servo Ventilator System", P. Bhansali, W. Cheong, G. Havashi and B. Rowley, *IEEE Transations on Biomedical Engineering*, BME-29, No. 8, Aug., 1982.

METHOD AND APPARATUS FOR CONTROLLING AN ARTIFICIAL RESPIRATOR

RELATED APPLICATION DATA

This is a continuation-in-part of U.S. patent application Ser. No. 178,019 filed Apr. 6, 1988 entitled "Method and Apparatus For Controlling An Artificial Respirator", now abandoned.

FIELD OF THE INVENTION

The present invention relates to a method and apparatus for controlling an artificial respirator. More particularly, the present invention relates to a method and apparatus for controlling a respirator based on the measured levels of carbon dioxide and oxygen of a patient on the respirator, as well as other physical conditions of the patient.

BACKGROUND OF THE INVENTION

Patients who have undergone surgery or who have certain respiratory diseases or paralysis often have problems. breathing properly and therefore must be provided with artificial respiration. The respirator used must be capable of being adjusted to provide the required amount of oxygen at an optimum frequency. The volume and frequency required not only varies with different patients, but can also vary within a single patient as the condition of the patient varies. In prior art respirators, changes must be made manually. This requires almost constant attention to the patient by a doctor or nurse, and the amount of change, when required, is effected by trial and error.

Attempts to provide automatic control of a respirator based on the condition of the patient have been described. One prior art system that has been described uses the concentration of carbon dioxide in the exhaust of the patient to control the operation of the respirator by switching the respirator on or off. See U.S. Pat. No. 4,537,190 to L. Caillot et al., issued Aug. 27, 1985, entitled "Process and Device for Controlling Artificial Respiration". See also, Y. Mitamura et al., "A dual control system for assisting respiration", MEDICAL & BIOLOGICAL ENGINEERING, Vol. 13, No. 6, pages 846-854. Other systems which have been described use both the concentration of carbon dioxide and oxygen in the exhaust, but these are used to control outputs of gas mixers, not outputs of an artificial respirator. See, e.g., M. H. Giard et al., "An Algorithm for Automatic Control of $O_2$ and $CO_2$ in Artificial Ventilation", IEEE TRANSACTION ON BIOMEDICAL ENGINEERING, Vol. BME-32, No. 9, September 1985, pages 658-667, and C. Yu et al., "Improvement in Arterial Oxygen Control Using Multiple-Model Adaptive Control Procedures", IEEE TRANSACTIONS ON BIOMEDICAL ENGINEERING Vol. BME-34, No. 8, August 1987, pages 567-574. However, all of these systems have problems in that they either do not take into consideration all of the relevant physical conditions of the patient or the techniques employed are directed toward controlling the output of the breathing gas supply rather than the artificial respirator.

SUMMARY OF THE INVENTION

A method and apparatus for automatically controlling a respirator includes first means receiving digital input data (from A/D converters coupled to $CO_2$ and $O_2$ sensors) representing the concentration of carbon dioxide and oxygen, respectively, in the exhaust of a patient using the respirator. The first means, which preferably comprises a programmable microcomputer, is controlled by a software algorithm to operate upon the input data and provide digital output data representing the amount and optimum frequency of ventilation required for the next breath. The microcomputer also operates upon additional data including metabolic rate ratio, lung elastance factor, air viscosity factor and barometric pressure to determine the magnitude of the digital output data. The value of the metabolic rate ratio is set to one and does not need to be monitored if the respirator is to be used on a patient who is under rest conditions. Only if the device is used on a patient in exercise should this factor, metabolic rate ratio, be monitored continuously and supplied by an additional monitor to the system via an input channel. The other additional data may be measured and entered manually (i.e., stored in the software or supplied through the input channels from fixed adjustable voltage sources) or additional sensors and monitors may be provided to supply this data to the system automatically. A second means converts the digital output data to analog data and a third means receives the analog data and regulates the ventilation frequency and volume and controls the opening and closing of valves coupled to the output of the respirator.

BRIEF DESCRIPTION OF THE DRAWINGS

For the purpose of illustrating the invention, there is shown in the drawings a form which is presently preferred; it being understood, however, that this invention is not limited to the precise arrangements and instrumentalites shown.

DETAILED DESCRIPTION OF THE PREFERRED EMBODIMENT

Figure 1:
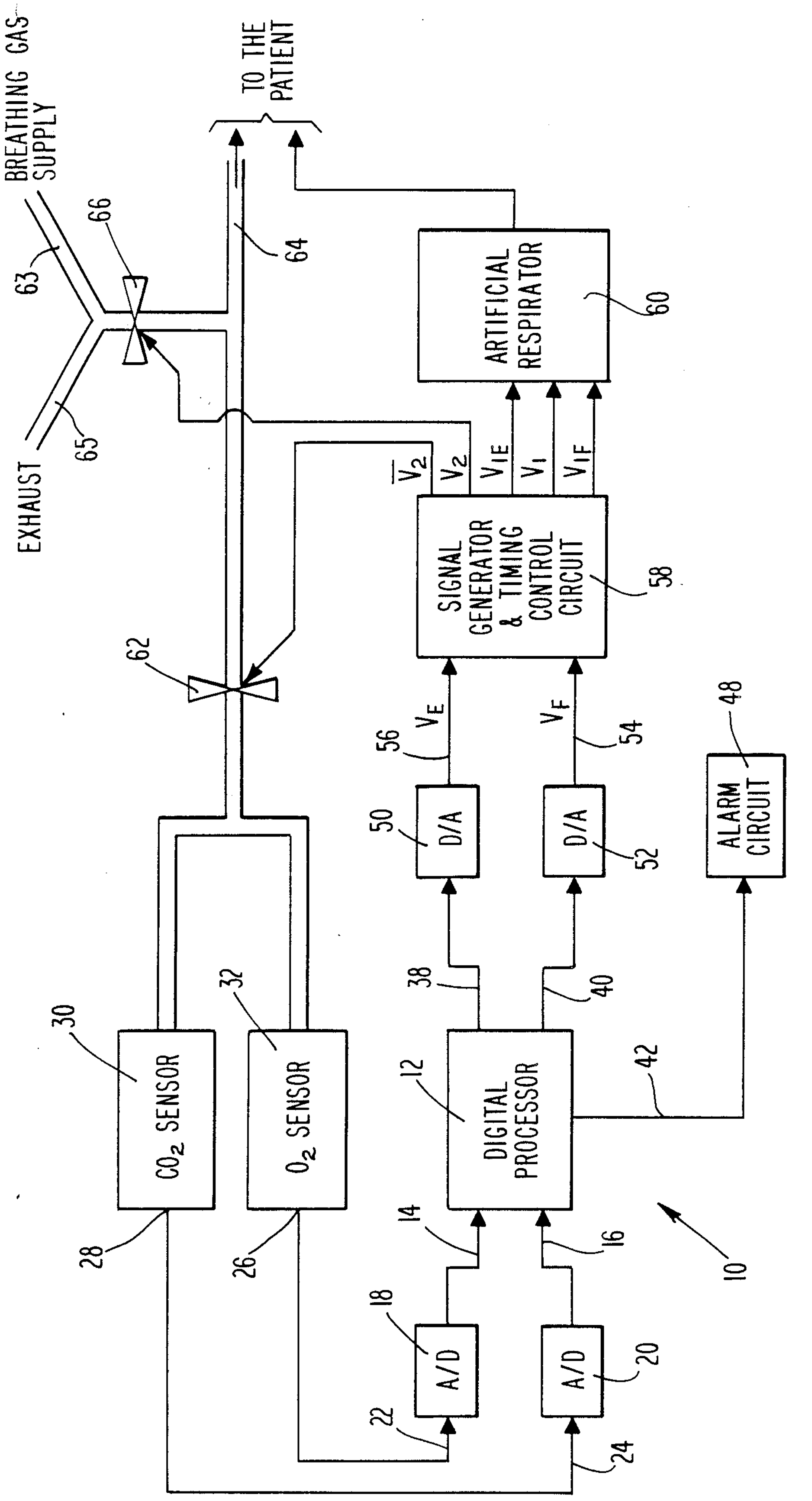
FIG. 1 is a block diagram of an artificial respirator and control apparatus according to the preferred practice of the present invention.

Referring to the drawings, wherein like numerals represent like elements, there is illustrated in FIG. 1 a respirator control according to the present invention, designated generally 10. Respirator control 10 includes a programmable controller 12 coupled to receive the outputs of eight bit A/D converters 18 and 20, as shown at 14 and 16. The A/D converters 18, 20 are preferably two channels of a Micromint brand eight bit eight channel A/D converter and the controller 12 is preferably a Micromint brand BCC52 BASIC controller. The inputs 22 and 24 of the two A/D converters 18, 20 are coupled to the outputs 26 and 28 of an oxygen sensor 32 and a carbon dioxide sensor 30, respectively. The additional channels of the A/D converter are reserved for additional data which can also be monitored continuously, including the patient's metabolic rate ratio, lung elastance, air viscosity factor in the lungs and barometric pressure. Lung elastance, air viscosity factor in the lungs and barometric pressure may be measured prior to operation of the device and supplied to the controller 12 through the reserved A/D channels or be stored in the software. If their values are supplied via the A/D converters, they can also be monitored continuously, if desired, using additional sensors and monitors (not shown). The value of the metabolic rate ratio does not need to be monitored when the patient is at rest. In this case, the value for metabolic rate ratio is set equal to one and stored in the software or an equivalent may be supplied through one of the reserved A/D channels to the controller 12. Only if the device is used in exercise should the metabolic rate ratio be monitored continuously using an additional analyser and supplied to the controller 12 through an A/D converter channel. Techniques and devices have been described for determining the rate of metabolism by measuring the oxygen uptake of the body. U.S. Pat. Nos. 4,572,208 and 4,368,740 are representative. But most of the described methods cannot be used to provide reliable data on a breath-by-breath basis. In the present invention, the oxygen uptake of the patient for every breath can be calculated by the controller 12 based on the values of alveolar ventilation and the concentrations of oxygen and carbon dioxide in the inspired and expired gas. But the rates of oxygen consumption and oxygen intake of the body are equal to each other only under steady state conditions. During transition periods in exercise, the oxygen uptake of the body does not reflect the rate of metabolism accurately and a metabolic rate monitor which uses other physical conditions (i.e., cardiovascular characteristics) of the patient should preferably be used to monitor the metabolic rate ratio and supply it to the controller 12. Referring again to the drawing, the A/D's 18, 20 constantly sample the $O_2$ and $CO_2$ sensor outputs (the output voltages from the sensors 30 and 32 vary between zero and five volts) and convert them to digital data.

Figure 2:
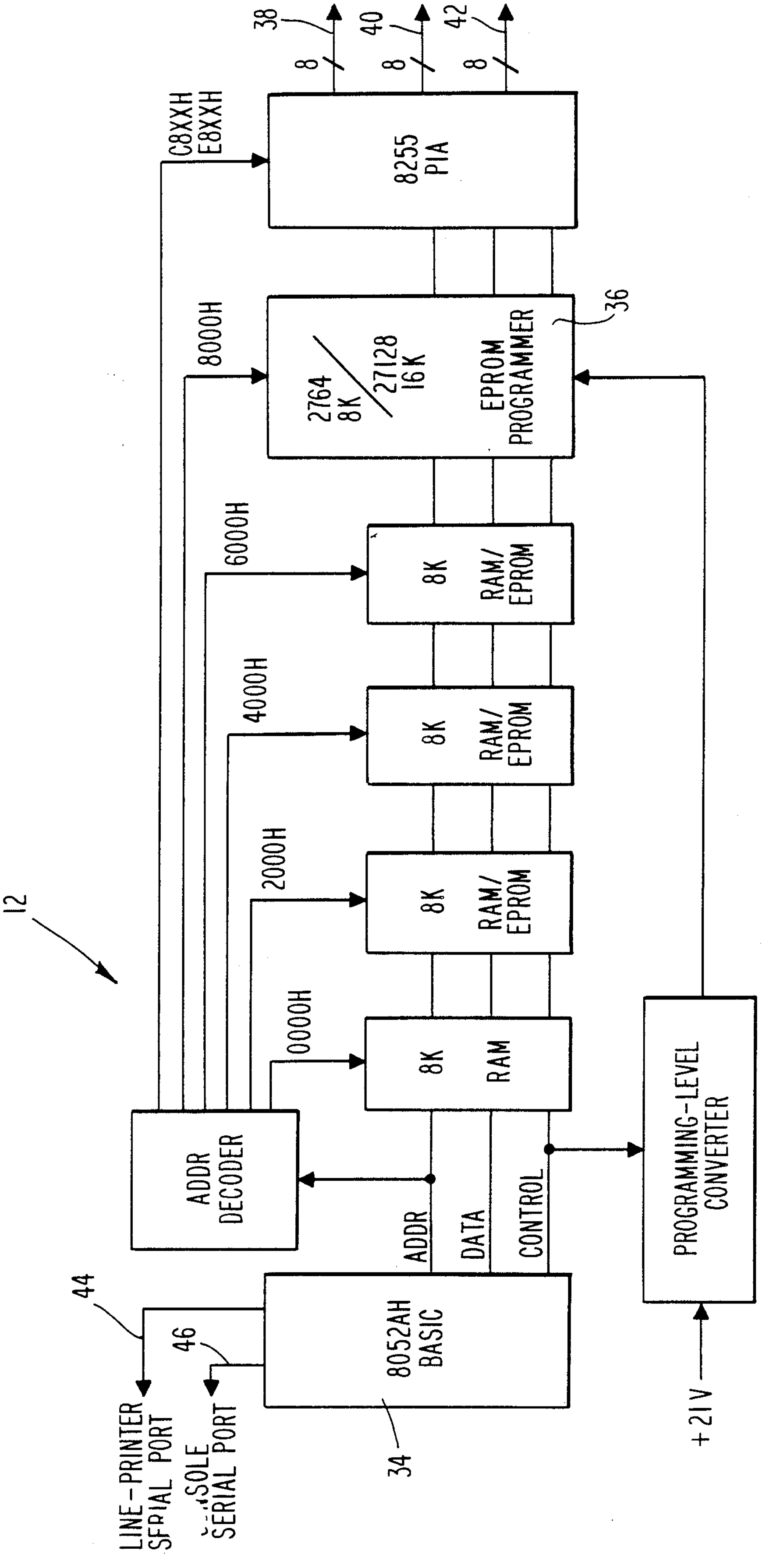
FIG. 2 is a block diagram of a programmable controller used in the preferred practice of the present invention.

As shown in FIG. 2, the controller 12 includes in the preferred embodiment: an Intel 8052AH-BASIC 8 bit microcomputer chip 34 which contains 8K bytes ROM as a basic interpreter; 48K bytes of RAM/EPROM; a 2764/27128 EPROM programmer 36, three parallel I/O ports 38, 40 and 42; a serial line printer port 44; and a serial terminal port 46. The 8052AH-BASIC microcomputer has a 16 bit address bus and an 8 bit data bus. The least eight significant address bits and the data bus are multiplexed together. In the method of the present invention, a control program is saved on a 2764 EPROM and is executed after resetting the controller at the beginning of the operation. The output port 42 of the controller 12 is connected to an alarm circuit 48. The output ports 38 and 40 are connected to D/A converters 50 and 52 respectively. The controller 12 receives the input data from the A/D converters 18 and 20 (and from the additional sensors and associated A/D's, if provided) and calculates the required ventilation and the optimum frequency for the next breath. It produces two signals, representing the total ventilation and the frequency of breathing which are converted to analog signals using the D/A converters 50 and 52.

The D/A converters 50 and 52 are preferably AM1408N8 eight bit D/A converters. The output voltage of these converters 50 and 52 varies from 0 to −5.8 volts for a load of 1Kohm. The outputs of the D/A converters 50 and 52 are fed to the input ports 54 and 56 of a signal generator and timing control circuit 58, which will be described in detail later. The signal generator and timing control circuit 58 produces five control signals. One of the signals ($V_1$) is a pulse whose amplitude is variable and corresponds to the desired level of ventilation; the pulse duration is only a fraction of the total breathing cycle and is switched to ground for the rest of the period. This signal ($V_1$) is used to control an artificial respirator 60. Another output ($V_2$) of the signal generator and timing control circuit 58 is a pulse having a fixed amplitude (i.e., the supply voltage), which remains high for a major portion of the breathing cycle. The complement of this pulse ($\overline{V}_2$) is provided to a control valve 62 coupled in the line 64 between the patient and the sensors 30 and 32. The control valve 62 controls the flow of the patient's exhaled gas to the sensors 30 and 32. The duration of the pulse $V_2$ is chosen to be a major portion of the breathing cycle to stop the flow of the exhaled gas which contains air trapped in the patient's anatomic dead space from passing through the sensors 30 and 32 during early stages of expiration. Pulse $V_2$ is provided to another control valve 66 which controls the flow of gas during inhalation and expiration. The inspiration line 63 and the exhaust line 65 have incorporated therein non-return valves (not shown), which are adapted to permit gas to flow solely in one direction (i.e., to the patient through line 63 and away from the patient through line 65). The signal generator and timing control circuit 58 produces two additional output signals (in the form of pulses) $V_{1E}$ and $V_{1F}$ which are provided to the respirator 60. The magnitude of signals $V_{1E}$ and $V_{1F}$ correspond to total ventilation and breathing frequency, respectively. Pulses $V_{1E}$ and $V_{1F}$ are the same as the signals $V_E$ and $V_F$ supplied to the signal generating and timing control circuit 58 from the D/A converters 50 and 5 if the controller is turned on. The signals $V_{1E}$ and $V_{1F}$ are generated by an adjustable voltage supply if the automatic controller is turned off.

The alarm circuit 48 comprises a NAND buffer (SN7400N) and four LEDs with series resistors, connected at the outputs of the buffer. See FIG. 5. The inputs to the buffer are provided from the output port 42 of the controller 12. Some of the LEDs are turned on if an alarm signal is transmitted to the output port 42.

Figure 4:
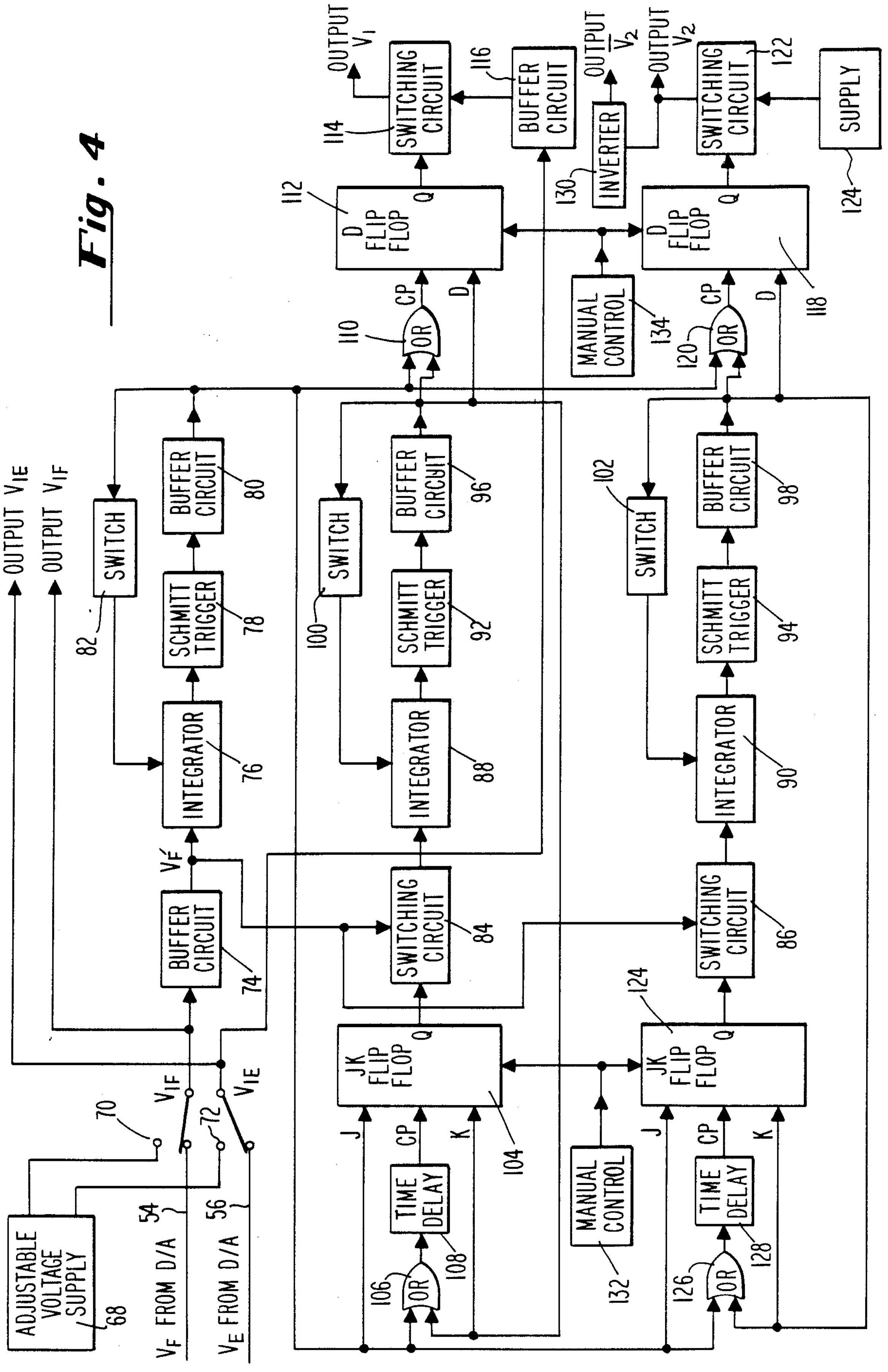
FIG. 4 is a detailed block diagram of a preferred circuit for controlling respirator and control valves.

Referring to FIG. 4, the signal generator and timing and control circuit 58 is illustrated in greater detail. The output signals $V_E$ and $V_F$ (on lines 56 and 54), representing the total ventilation and the breathing frequency, respectively, are provided to circuit 58. An adjustable voltage supply 68 is connected to the output lines 54 and 56 through switches 70 and 72. The switches 70 and 72 switch the circuit 58 to the voltage supply 68 when the automatic controller is turned off. The load resistance for the D/A converters 50 and 52 should be 1Kohm. A buffer circuit 74 is coupled to an integrator circuit 76. The output of the integrator circuit 76 is a periodic ramp function which triggers a Schmitt trigger circuit 78 when its amplitude reaches its maximum value. The output of the Schmitt trigger circuit 78 is either 1.8 volts or 12 volts. In order to decrease the amplitude of this voltage, a buffer circuit 80 is used. The output of the buffer circuit 80 activates (closes) a switch 82 when it goes high. The closure of switch 82 forces the output of the integrator circuit 76 to its low value just after its maximum value is reached. At this point the output of the Schmitt trigger circuit 78 and the buffer circuit 80 go low and the switch 82 opens. Since the magnitude of the output of the buffer circuit 74 ($V_F$) corresponds to the breathing frequency, the period of the ramp function generated at the output of the integrator circuit 76 is the same as the period of the breathing cycle.

The output of the buffer circuit 74 is also connected to switching circuits 84 and 86 which in turn are connected to integrator circuits 88 and 90 respectively. The integrator circuits 88 and 90 are connected to Schmitt trigger circuits 92 and 94 respectively, and the Schmitt trigger circuits 92 and 94 are connected to buffer circuits 96 and 98 respectively. Switches 100 and 102 are connected between the buffer circuits 96 and 98 respectively and the integrator circuits 88 and 90 respectively.

The level of the output of the switching circuit 84 is the voltage output of the buffer circuit 74 ($V_F$) when its input is high and is at ground level otherwise. The input of the switching circuit 84 is the output (Q) of a J-K flip flop 104. The J input of the flip flop 104 is coupled to the output of the buffer circuit 80. The K input of the flip flop 104 is coupled to the output of the buffer circuit 96. The signals provided to the J and K inputs of flip flop 104 are also provided as inputs to an OR gate 106 having an output delayed by a time delay 108. The output of the time delay 108 provides the clock pulse for the flip flop 104. Depending upon the propagation delay of the OR gate 106, the time delay 108 may be needed to provide the set up time for the J and K inputs before the arrival of the clock pulse. At the beginning of every breathing cycle, there is a pulse at the output of the buffer circuit 80 which also appears at the J input of the flip flop 104 forcing the Q output of the flip flop to go high. As a result, the output of the switching circuit 84 will be switched to $V_F$ and the integrator circuit 88 begins generating a voltage ramp. When the voltage of the ramp reaches the threshold voltage of the Schmitt trigger circuit 92, the output of the Schmitt trigger circuit 92 and the buffer circuit 96 go high, the switch 100 is activated, and the output of the integrator circuit 88 is forced to its low level. At the same time, since the K input to the flip flop 104 is pulsed high while the J input is low, the Q output of the flip flop circuit 104 is forced to logic "0". A logic "0" at Q produces zero voltage at the output of the switching circuit 84 and at the input of the integrator circuit 88. Therefore, the output of the integrator circuit 88 remains at its low level until another pulse is generated at the output of the buffer circuit 80 at the beginning of the next breathing cycle, and output Q of the flip flop 104 goes high.

The outputs of the two buffer circuits 80 and 96 are the inputs to an OR gate 110. The output of buffer circuit 96 is the input to a D flip flop 112. The output of the OR gate 110 is the clock pulse for flip flop 112. The Q output of the flip flop 112 is the input to a switching circuit 114. The output $V_1$ of the switching circuit 114 is at $-V_{1E}$ when its input is low and is at ground level otherwise. A buffer circuit 116 is provided to keep the load resistance of the D/A converter at 1Kohm. As mentioned, $V_{1E}$ is the output of a D/A converter if the automatic controller is on. The output of the integrator circuit 88 is a ramp function during a fraction of the breathing cycle. This fraction is controlled by choosing the appropriate components in the integrator circuit 88. During the rest of the cycle, the output of the integrator circuit 88 is at its low level because its input is switched to ground. When the threshold level for the Schmitt trigger 92 is reached, a pulse is generated at the output of the buffer circuit 96. Therefore the output Q of the flip flop 112 is forced to logic "1" and the output $V_1$ is switched to ground. At the beginning of the next breathing cycle, a pulse is generated at the output of the buffer 80. At this point the flip flop 112 is clocked while its D input is low. Therefore, the Q output of flip flop 112 goes to logic "0" and $V_1$ is switched to $-V_{1E}$. This cycle is repeated for every breath. Output $V_1$ is a variable amplitude periodic pulse signal whose amplitude at $-V_{1E}$ is directly proportional to total ventilation; its period is the same as the period of the breath. The pulse width is a fraction of the breathing period (i.e., 40%). This adjustable fraction represents the inspiratory time (%) and is controlled by the integrator circuit 88. $V_1$ is a control signal for the artificial respirator.

The integrator circuit 90 generates another timing control signal ($V_2$). The output of the buffer 98 is provided to the D input of a D flip flop 118. The outputs of buffers 80 and 98 are provided to the inputs of an OR gate 120 which generates the clock pulse for the flip flop circuit 118. The output Q of the flip flop circuit 118 is provided to the input of a switching circuit 122. The output of the switching circuit 122 ($V_2$) is at the supply voltage level when its input is low and is at ground level otherwise. The input to the integrator circuit 90 is provided from the output of the switching circuit 86. The output of the switching circuit 86 is at $V_F$ if its input is high and is at ground level otherwise. The input to the switching circuit 86 is provided from the output Q of a J-K flip flop 124. The J and K inputs of the flip flop 124 are coupled to the outputs of the buffers 80 and 98 respectively. These two signals are also coupled to the inputs of an OR gate 126 whose output provides the clock pulse for the flip flop 124 after being delayed by a time delay circuit 128 if necessary. The delay may be needed to provide the set up time for the J and K inputs of the flip flop 124.

At the beginning of every breath, a pulse is generated at the output of the buffer circuit 80. Therefore, a pulse arrives at the J input of flip flop 124 which forces the Q output of the flip flop 124 to logic "1". A logic "1" at the input of switching circuit 86 produces the voltage $V_F$ at the input of the integrator circuit 90. When the output of integrator circuit 90, which is a ramp function, reaches the threshold level of the Schmitt trigger circuit 94, a pulse is generated at the output of the Schmitt trigger circuit 94 and at the output of the buffer circuit 98. At this point switch 102 is activated (closed) and the output of the integrator circuit 90 goes low. At the same time, a pulse is provided to the K input of flip flop 124 and to the D input of flip flop 118. The Q output of flip flop 124 is forced to logic "0". A logic "0" at the input of the switching circuit 86 produces zero volts at the input of the integrator circuit 90. Consequently, the output of the integrator circuit 90 remains low for the rest of the breathing cycle. Also, a pulse at the D input of the flip flop 118 forces the Q output of the flip flop 118 to logic "1". A logic "1" at the input of the switching circuit 122 produces zero volts at the output of the switching circuit 122. Therefore, the output voltage $V_2$ at the switching circuit 122 remains low until another pulse is generated at the output of buffer 80 at the beginning of the next breathing cycle. At this point, since a pulse has appeared at the J input of flip flop 124, output Q of the flip flop 124 goes high, the output of switching circuit 86 is switched to $V_F$ and the output of the integrator circuit 90 begins ramping. Also, at the same time, a pulse is generated at the output of the OR gate 120 and the flip flop 118 is clocked while its D input is low. Therefore, the output Q of flip flop 118 is forced to logic "0" and signal $V_2$ is switched to the supply voltage. This cycle is repeated for every breath. Output $V_2$ is a periodic pulse signal which is at the voltage supply level at the beginning of every breathing cycle and remains at this level during only a fraction of the cycle; the fractional amount is adjustable and is controlled by the integrator circuit 90. $V_2$ and its complement (from inverter 130) are used to control the valves 66 and 62; the control valves 62 and 66 control the flow of the patient's exhaust gas to the sensors 30 and 32. The duration of the pulse $V_2$ is chosen to be a major portion of the breathing cycle (i.e., 65%) to prevent the flow of exhaust gas from the patient's dead space volume through the sensors 30 and 32 at the beginning of expiration. Circuits 132 and 134 are two manual control circuits for the flip flops. Manual control circuit 132 controls J-K flip flops 104 and 124, and manual control circuit 134 controls the D flip flop circuits 112 and 118. At the beginning of operation, the preset inputs of flip flops 104 and 124 and the clear inputs of flip flops 112 and 118 are activated. The flip flop circuits 104, 112, 118 and 124 are positive edge triggered type flip flops.

Figure 5A:
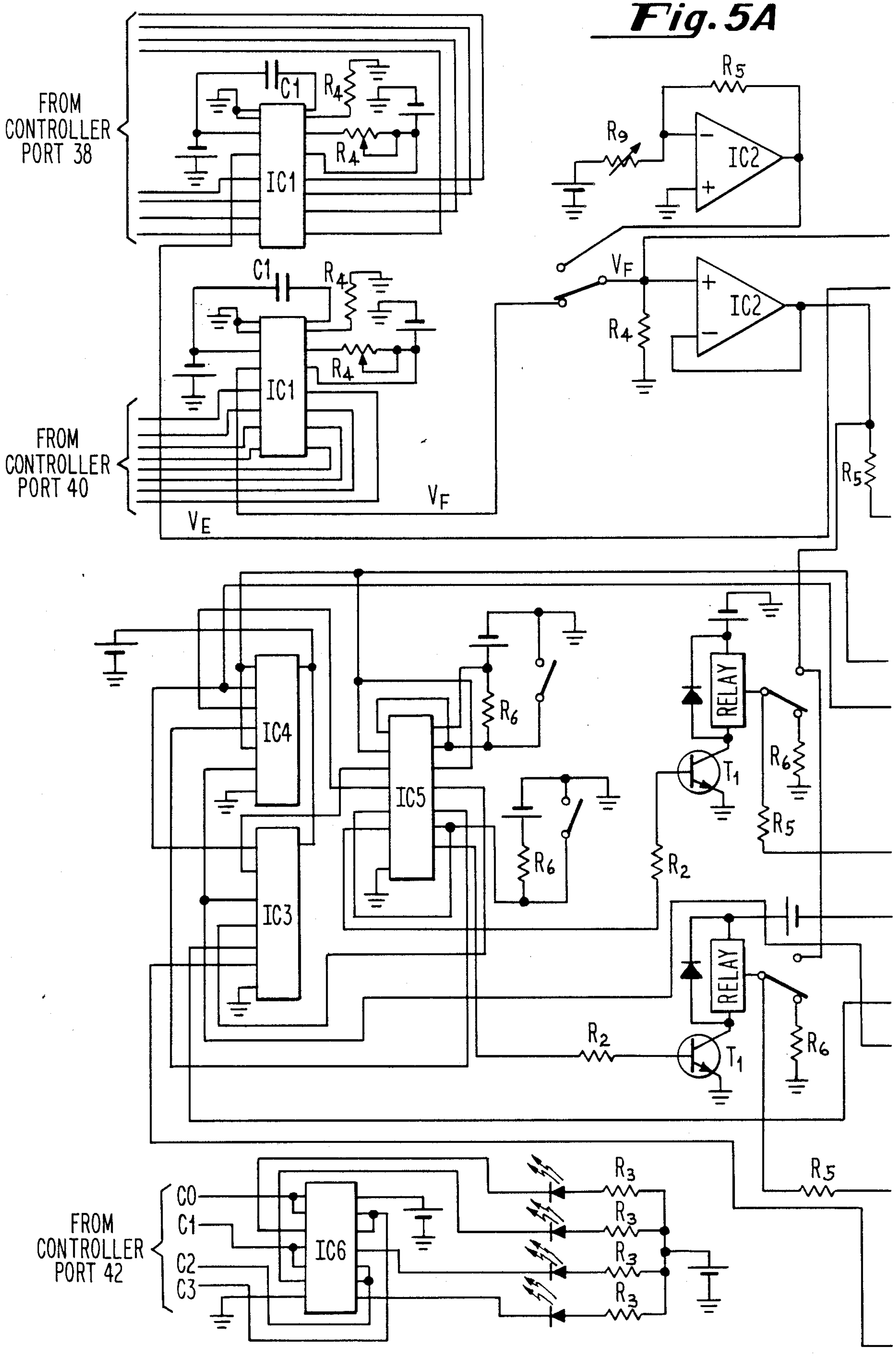
FIGS. 5A-5B are a preferred detailed schematic diagram of a signal generator and timing control circuit, including D/A converters and an alarm circuit, for use in the practice of the present invention.
Figure 5B:
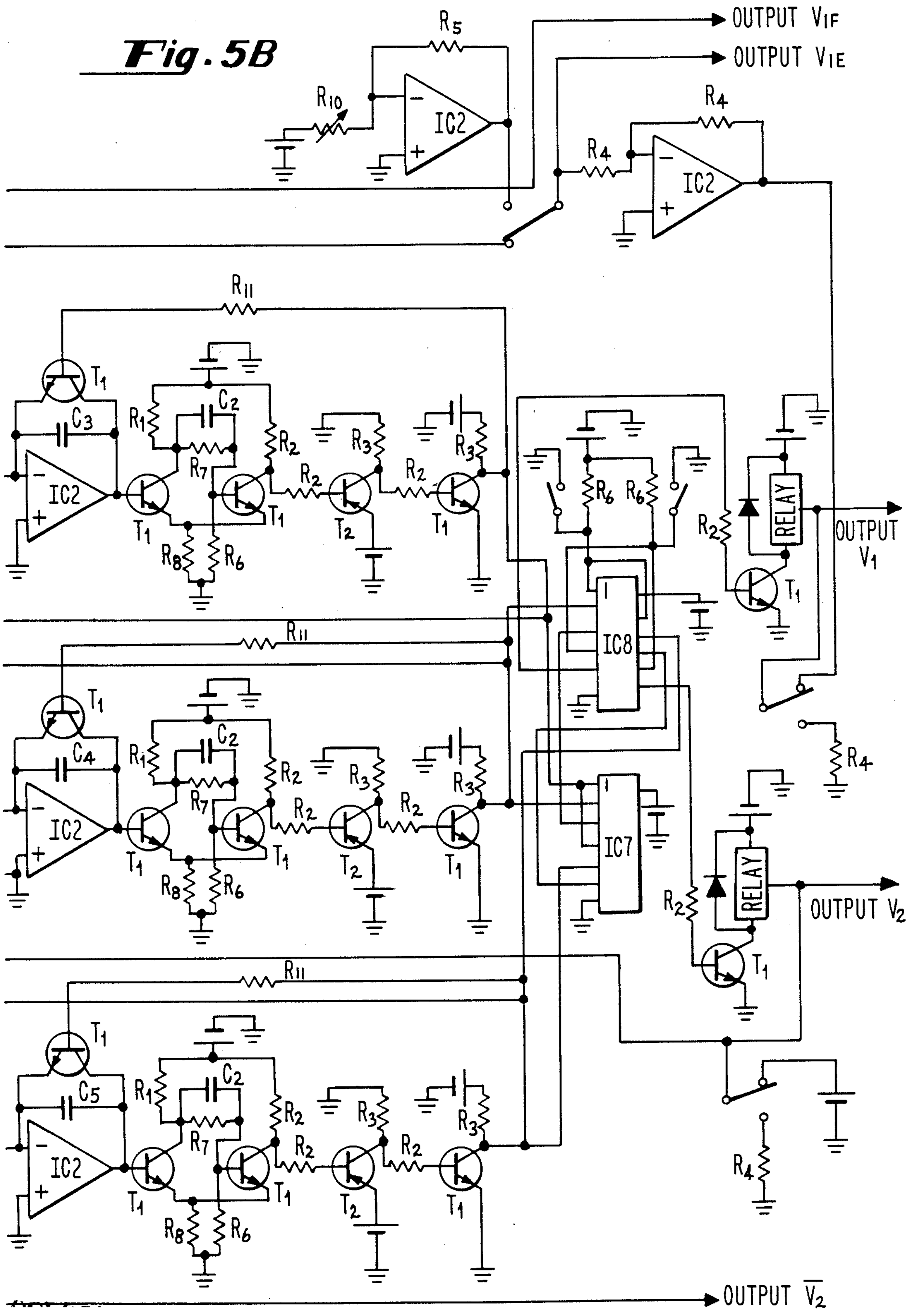

FIG. 5 illustrates in detail the preferred circuit diagram of the D/A circuits 50 and 52, the signal generator and timing control circuit 58 and the alarm circuit 48. The preferred component types and values are set forth in the chart below.

| | | | |
|---|---|---|---|
| IC1 | AM14088N | C5 | 1.3 mf |
| IC2 | 741CN | R1 | 2.2 Kohm |
| IC3 | SN7404N | R2 | 5.6 Kohm |
| IC4 | MC14071 | R3 | 330 ohm |
| IC5 | SN74LS109AN | R4 | 1 Kohm |
| IC6 | SN7400N | R5 | 12 Kohm |
| IC7 | SN7432N | R6 | 10 Kohm |
| IC8 | DM7474J | R7 | 22 Kohm |
| T1 | 2N222 | R8 | 680 ohm |
| T2 | 2N4403 | R9 | 5-50 Kohm |
| C1 | 11 pf | R10 | 10-50 Kohm |
| C2 | 180 pf | R11 | 56 Kohm |
| C3 | 2 mf | Relay | HA1-Aromat |
| C4 | 0.8 mf | | |

Figure 3A:
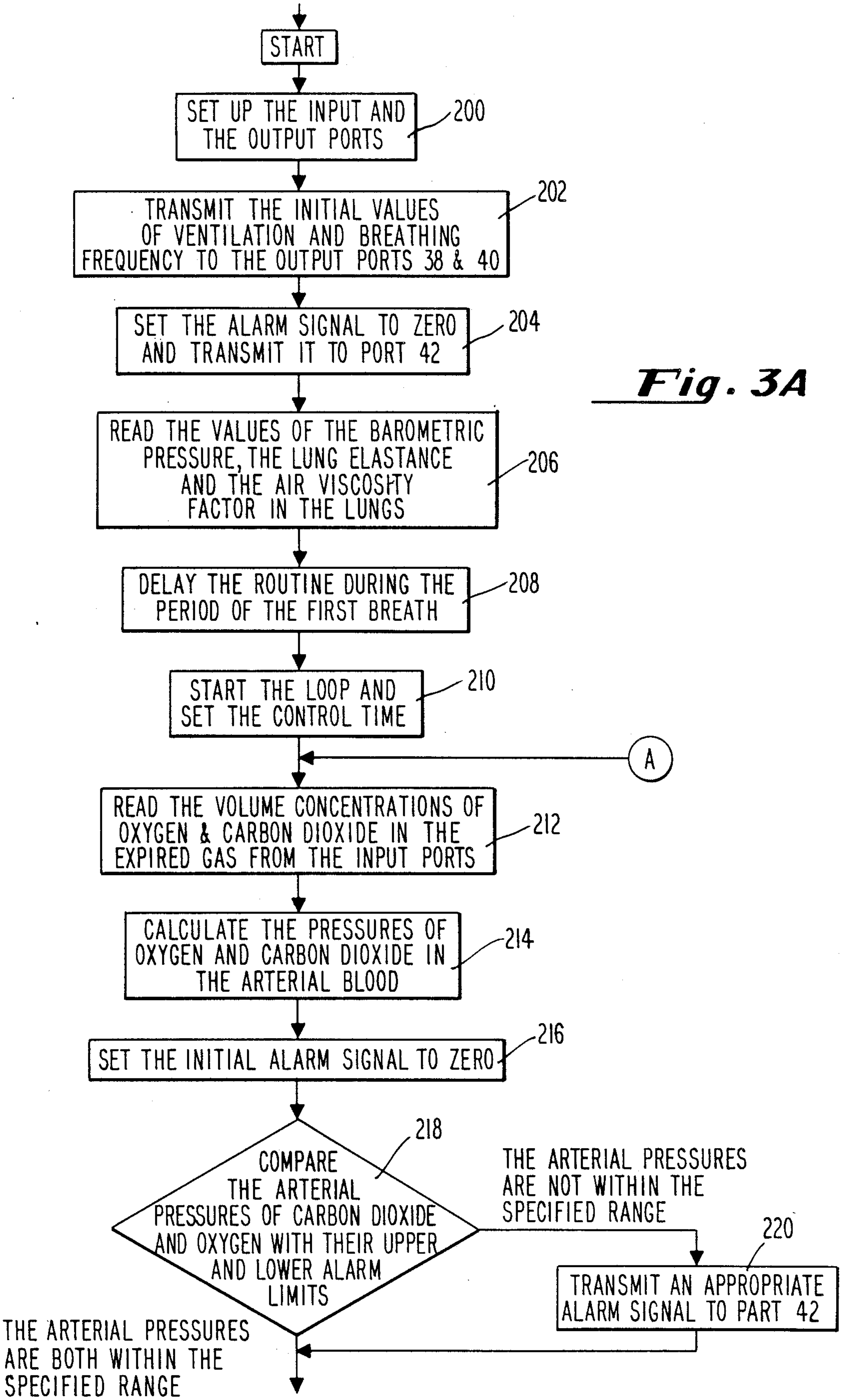
FIGS. 3A-3C are a flow chart illustrating the preferred sequence of steps executed by the programmable controller for carrying out the method of the present invention.
Figure 3B:
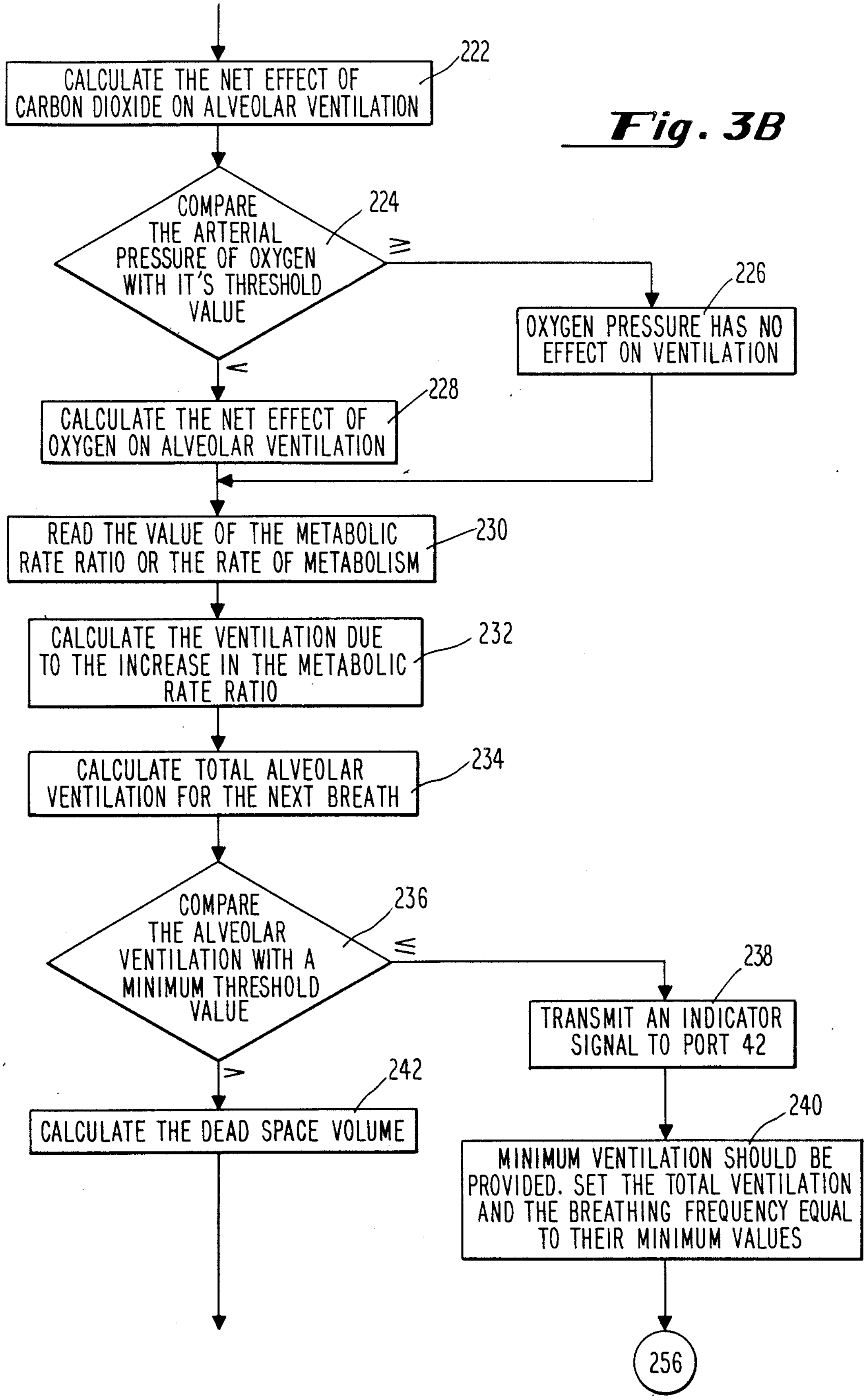
Figure 3C:
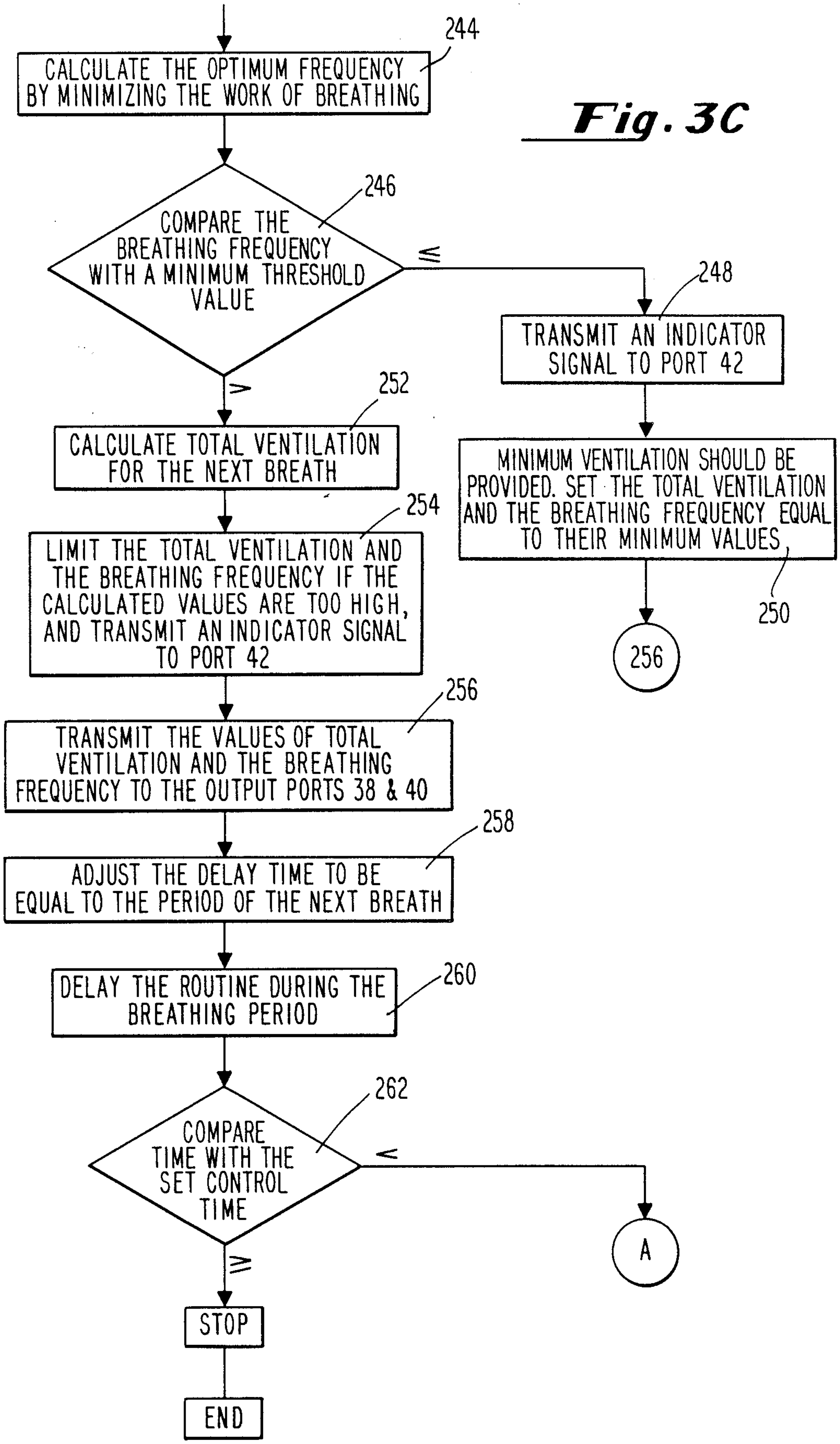

Referring to FIGS. 3A-3C, there is illustrated a flow chart of the sequence of steps to be performed by the controller 12 in the preferred practice of the method of the present invention. Those skilled in the art will appreciate that the illustrated sequence of steps may be easily reduced to source code instructions for input to and execution by the microcomputer 34. As can be seen at the start of the flow chart, after having set up the input and the output ports at 200, initial values for ventilation and the breathing frequency are provided to the output ports 38, 40 of controller 12, as shown at 202. The alarm (coupled to port 42 of controller 12) is reset as shown at 204. Values representing lung elastance factor, air viscosity factor in the lung and barometric pressure are read from the input ports or from the memory (if stored in the software) as shown at 206. (Alternatively, if monitors for continuous measurement of these data are provided, then the controller reads these data from those monitors via the input ports preferably during execution of the loop illustrated at A). At step 208, the program routine is delayed for the interval of the first breath (specified at 20 by the initial value of the breathing frequency). A program loop and control time for executing the loop are entered as shown at 210. Once the loop is entered, the volume concentrations of carbon dioxide and oxygen in the exhaled gas are read from the input ports as shown at 212.

The next step, shown at 214, is to calculate the pressures of oxygen and carbon dioxide in the patient's arterial blood. This is calculated according to the following equations:

$$P_{ACO2}=C_{co2}\times(P_B-47),\ P_{aco2}=P_{ACO2}-K_1$$

$$P_{AO2}=C_{o2}\times(P_B-47),\ P_{ao2}=P_{AO2}-K_2$$

where $P_{ACO2}$ and $P_{AO2}$ are the partial pressures of $CO_2$ and $O_2$ in the alveolar space, $C_{co2}$ and $C_{o2}$ are the volume concentrations of $CO_2$ and $O_2$ in the exhaled gas, $P_B$ is the barometric pressure (mmHg), and

47 is the partial pressure in mmHg of water vapor in the alveolar space.

$P_{aco2}$ and $P_{ao2}$ are the pressures of $CO_2$ and $O_2$ in the arterial blood, $K_1$ and $K_2$ are two constants representing the average differences between the alveolar and arterial pressures of $CO_2$ and $O_2$ in mmHg respectively.

As shown at 216, the initial alarm signal is set to zero (deactivated), and the calculated $P_{aco2}$ and $P_{ao2}$ values are compared to upper and lower alarm limits (i.e., 46 mmHg and 25 mmHg for $P_{aco2}$ and 140 mmHg and 60 mmHg for $P_{ao2}$) as shown at 218. If either of the pressures is outside the specified range, an appropriate alarm signal is generated and provided to the alarm via port 42 as shown at 220, and the step illustrated at 222 is performed. If both pressures are within their specified ranges, then no alarm is generated and the step illustrated at 222 is next performed. At step 222, the net effect of $CO_2$ concentration on ventilation requirements is calculated according to following equation:

$$V_c=0.405\times P_{aco2}-14.878$$

where $V_c$ is the ratio of alveolar ventilation as the net effect of $CO_2$ to the resting value of ventilation.

Next, as illustrated at 224, the arterial pressure of oxygen, $P_{ao2}$, is compared to a threshold value of 104 mmHg. If the value of $P_{ao2}$ is greater than or equal to the threshold value, the effect of oxygen on ventilation is zero (step 226), and program control passes to step 230. If, on the other hand, the value of $P_{ao2}$ is less than the threshold value, then step 228 is performed and the net effect of $P_{ao2}$ on ventilation requirements is calculated according to the following equation:

$$V_o=(4.72\times10^{-9})\times(104-P_{ao2})^{4.9}$$

where $V_o$ is the ratio of alveolar ventilation as the net effect of oxygen to the resting value of ventilation.

At step 230, the rate of metabolism or the metabolic rate ratio (rate of metabolism/basal rate of metabolism) is read by the controller. This value is either read from the memory or from an input port. The metabolic rate ratio is set equal to one and stored in the software or supplied through an input channel if the respirator is to be used under rest conditions. This value does not need to be monitored when the patient is at rest. When the patient is in exercise, the metabolic rate ratio (or the rate of metabolism) should be monitored continuously and supplied via an input channel.

The next step, illustrated at 232, is to calculate the effect of increasing the metabolic rate ratio on ventilation. This facilitates the use of artificial respirators in exercise, if necessary, and is particularly useful if the metabolic rate ratio is monitored continuously. The following equation, derived from experimentation in exercise, is used to calculate the net effect of metabolic rate ratio on ventilation:

$$V_M = 0.988(MRR - 1)$$

where $V_M$ is the ratio of alveolar ventilation as the net effect of increase in the rate of metabolism to the resting value of ventilation, and MRR represents the metabolic rate ratio (rate of metabolism/basal rate of metabolism).

In the next step, illustrated at 234, total alveolar ventilation for the next breath is calculated according to the following equation:

$$V_A = V_A(\text{at rest}) \times (V_c + V_o + V_M)$$

where $V_A$ is the alveolar ventilation in liters/minute.

Next, as shown at 236, the calculated value for $V_A$ is compared with a minimum threshold of 1.35 liters/minute. If $V_A$ is less than or equal to this threshold value, total ventilation and breathing frequency are set to minimum (2.3 liters/min. and 6 breaths/min., respectively) and an alarm is generated, as shown at 238, 240. Thereafter, program control turns to step 256 of the loop in FIG. 3C where the values of minute ventilation and breathing frequency are transmitted to output ports 38 and 40. If, however, at step 236, the value of $V_A$ is determined to be greater than the minimum threshold value, then step 242 is performed. At step 242, the patient's dead space volume is determined.

The dead space volume increases with alveolar ventilation. The following equation has been derived from experimental data and from published relationships between expired volume, alveolar ventilation and dead space volume:

$$V_D = \frac{0.1698}{60} \times V_A + 0.1587$$

where $V_D$ is the dead space volume in liters.

As illustrated at 244, the next step is to calculate the optimum frequency for the next breath; this is determined on the basis of minimum work criterion. The work performed during respiratory action can be described by the following equation:

$$W = \int P dv' = \int K' v' dv' + \int K'' dv'(dv'/dt)$$

In the above equation, W is the work of breathing, P is the total pressure necessary to overcome the resistive forces existing in the respiratory system, v, is the difference between the lung volume and the functional residual capacity, K, is lung elastance, K" is the air viscosity factor in the lungs, and t is time. This equation can be differentiated with respect to time and rewritten as follows:

$$dw = K'v'(dv'/dt)dt + K''(dv'/dt)^2 dt$$

Assuming that the air flow rate has a sinusoidal waveform ($dv'/dt = a \sin \Omega t$) and ignoring the expiratory work, the total work of the respiratory action can be found:

$$W = 0.5K'V_T^2 + 0.25\ K''fV_T^2 \times \pi^2$$

where $V_T$ is the tidal volume. Mean rate of work W. (W. =Wf) can then be expressed as a function of the tidal volume:

$$W. = Wf = 0.5K'fV_T^2 + 0.25K''f^2V_T^2 \times \pi^2$$

where $V_T = (V_A/60f) + V_D$

Therefore:

$$W. = 0.5K'f(V_{AR}/f + V_D)^2 + 0.25K''f^2\pi^2 \cdot (V_{AR}/f + V_D)^2$$

where $V_{AR}$ is the alveolar ventilation in liters/second ($V_{AR} = V_A/60$).

By differentiating the above equation for W. with respect to frequency and setting the resulting equation equal to zero, the optimum frequency of breathing for minimum work can be found. The resultant equation is as follows:

$$f = \frac{-K'V_D + \sqrt{(K'V_D)^2 + 4K'K''\pi^2 V_{AR} V_D}}{2\pi^2 V_D K''}$$

This equation has been used to calculate the optimum frequency of breathing for every breath in the controller 12 (f is in cycles/second).

Next, as shown at 246, frequency (f) is compared with a minimum threshold value of 6 breaths/minute. If the value of f is less than or equal to this threshold value, ventilation and frequency are set to minimum and an alarm signal is generated, as shown at 248 and 250. Program control thereafter turns to step 256 of the program. If, however, the value of f is greater than the minimum threshold value, the next step, 252, is performed. At 252, total ventilation is calculated according to the following equation:

$$V_E = V_A + 60fV_D$$

where $V_E$ represents total ventilation in liters/minute.

At step 254, total ventilation and frequency are compared with their upper limit values. If they happen to be too high, their values are limited and an alarm is generated.

At step 256, two digital signals representing $V_E$ (total ventilation), and f (frequency) for the next breath are transmitted to the output ports 38, 40. At step 258, a delay interval is adjusted to be equal to the period of the next breath and, at step 260, the program routine is delayed for this interval. After the delay interval expires, running time is compared with the control time, as shown at 262. If the running time is less than the total control time, program control returns to A in FIG. 3A. The total control time is an arbitrary value which is specified at the beginning of the program. If the running time is greater than or equal to the control time, the procedure is stopped. During the running period, the automatic controller can be turned off and respirator control can be switched to manual control at any time, if needed. In the manual control mode, the minute ventilation and the frequency of every breath or alternatively the positive end expiratory pressure "peep" is specified for the respirator by an operator. The end expiratory pressure may also be continuously monitored by additional sensors through the reserved channels of the A/D converter. A system reset is required to restart the controller.

There has been described an apparatus and method for automatically measuring the concentration of carbon dioxide and oxygen in the exhaust of a patient and using this and other physiologic data to automatically control the breathing frequency and volume of gas delivered by the respirator. The present invention may be embodied in other specific forms without departing from the spirit or essential attributes thereof, and accordingly, reference should be made to the appended claims rather than to the foregoing specification, as indicating the scope of the invention.

What is claimed is:

1. In a respirator for varying tidal volume and frequency of breaths of a patient, an apparatus for automatically controlling the respirator comprising:

first means for processing data representing at least air viscosity factor in lungs of the patient, barometric pressure, lung elastance factor of the patient and measured levels of carbon dioxide and oxygen levels of the patient, and for providing, based upon said data, digital output data indicative of required ventilation and optimum frequency for a next breath of the patient;

second means operatively coupled to the first means for converting the digital output data to analog data; and, third means operatively coupled to the second means and to the respirator for converting the analog data to timing and control signals and supplying the timing and control signals to the respirator, the timing and control signals automatically and variably controlling the tidal volume and frequency of inhaled gas provided to the patient by the respirator based upon actual ventilation and breathing frequency requirements of the patient as determined by the first means.

2. Apparatus in accordance with claim 1 including A/D converters connected to an input of said first means for converting analog signals from carbon dioxide and oxygen sensors, representing concentrations of carbon dioxide and oxygen in exhaled gas of the patient, to digital data.

3. Apparatus in accordance with claim 2 in which the first means comprises a programmable microcomputer.

4. Apparatus in accordance with claim 3 further comprising program means for determining from the digital input data (i) the partial pressures of carbon dioxide and oxygen in the alveolar space of the patient, (ii) the patient's arterial pressures of carbon dioxide and oxygen, (iii) the net effect of carbon dioxide and oxygen on alveolar ventilation, and (iv) the total alveolar ventilation required for the patient's next breath.

5. Apparatus in accordance with claim 4 in which the third means comprises means for providing a first pulse for controlling the respirator, the first pulse having a variable amplitude corresponding to the level of required ventilation and having a duration that is only a fraction of the breathing cycle, this fraction representing an inspiratory time (%), means for providing a second pulse for controlling the valves, the second pulse having a constant amplitude and a duration for a major portion of the breathing cycle, and means for providing two additional pulses for controlling the respirator, the two additional pulses corresponding to total minute ventilation and breathing frequency respectively.

6. Apparatus in accordance with claim 5 wherein the means for providing each of said first and second pulses comprises a separate circuit including a switching circuit receiving an analog data signal from the second means, an integrator circuit connected to the output of the switching circuit, a Schmitt trigger circuit connected to the output of the integrator circuit, a buffer circuit connected to the output of the Schmitt trigger circuit and a switching circuit coupled between the output of the buffer circuit and a control input of the integrator circuit.

7. Apparatus in accordance with claim 6 wherein the two additional pulses are provided as inputs to the third means.

8. Apparatus according to claim 1 wherein the data representing air viscosity factor in the lungs, barometric pressure and lung elastance factor are entered manually and stored in a software program.

9. Apparatus according to claim 1 wherein the data representing air viscosity factor in the lungs, barometric pressure and lung elastance are supplied via A/D channels to the first means.

10. Apparatus according to claim 9 wherein the data representing air viscosity factor in the lungs, barometric pressure and lung elastance factor is provided to the first means by monitors coupled to measure the same.

11. Apparatus according to claim 1 wherein the first means also receives and processes data representing metabolic rate ratio.

12. Apparatus according to claim 11 wherein, when the patient is at rest, a predetermined value representing metabolic rate ratio is supplied to the first means.

13. Apparatus according to claim 12 wherein the predetermined value representing metabolic rate ratio is stored in a memory.

14. Apparatus according to claim 12 wherein the predetermined value representing metabolic rate ratio is supplied via an A/D to the first means.

15. Apparatus according to claim 11 wherein, when the patient is in exercise, a value representing metabolic rate ratio is supplied from a metabolic rate monitor.

16. In a respirator for varying tidal volume and frequency of breaths of a patient, a method of automatically controlling the respirator comprising the steps of:

(a) measuring levels of carbon dioxide and oxygen of the patient and providing a first pair of data signals indicative of the same;

(b) providing data indicative of at least the patient's lung elastance factor, air viscosity factor in the lungs and barometric pressure;

(c) determining from said first pair of data signals and from the data provided in step (b) the required ventilation and breathing frequency for a next breath of the patient and providing a second pair of data signals indicative of the same; and, (d) providing, based upon said second pair of data signals, final data signals for automatically and variably controlling the ventilation and breathing frequency of the respirator based upon actual ventilation and breathing frequency requirements of the patient as determined in step (c).

17. A method in accordance with claim 16 wherein the first pair of data signals are in analog form and are converted to digital form before providing said second pair of signals, and the second pair of signals are converted from digital form to analog form before providing said final signals.

18. A method in accordance with claim 17 wherein the value of the data signal representing the ventilation is obtained by determining, (i) from the values of said first pair of data signals, the partial pressures of carbon dioxide and oxygen in the alveolar space of the patient, (ii) from partial pressures of carbon dioxide and oxygen, the patient's arterial pressures of carbon dioxide and oxygen, (iii) from the arterial pressures of carbon dioxide and oxygen, the net effect of carbon dioxide and oxygen on alveolar ventilation and (iv) the total ventilation for the next breath based upon the value of the one of the second pair of data signals corresponding to the total alveolar ventilation.

19. A method in accordance with claim 18 wherein the arterial pressures of carbon dioxide and oxygen are determined according to the following relationships:

$$P_{ACO2}=C_{co2}\times(P_B-47),\ P_{aco2}=P_{ACO2}-K_1$$

$$P_{AO2}=C_{o2}\times(P_B-47),\ P_{ao2}=P_{AO2}-K_2$$

where $P_{ACO2}$ and $P_{AO2}$ are the partial pressures of $CO_2$ and $O_2$ in the alveolar space, $P_B$ is the barometric pressure in mmHg, 47 is the partial pressure in mmHg of water vapor in the alveolar space, $C_{co2}$ and $C_{o2}$ are volume concentrations of $CO_2$ and $O_2$ in the exhaled gas of the patient, $P_{aco2}$ and $P_{so2}$ are the arterial pressures of $CO_2$ and $O_2$ and $K_1$ and $K_2$ are two constants representing the average differences between the alveolar and arterial pressures of $CO_2$ and $O_2$ in mmHg, respectively.

20. A method in accordance with claim 19 wherein the net effect of carbon dioxide and oxygen are determined according to the following relationships:

$$V_c=0.405\times P_{aco2}-14.878$$

$$V_o=(4.72\times 10^{-9})\times(104\times P_{ao2})4.9$$

where $V_c$ and $V_o$ represent the ratios of alveolar ventilation as the net effects of carbon dioxide and oxygen respectively to the resting value of ventilation.

21. A method in accordance with claim 20 wherein data indicative of the patient's metabolic rate ratio is also provided and the total alveolar ventilation is determined according to the following relationship:

$$V_A=V_A\text{ (at rest)}\times(V_c+V_o+V_M)$$

where $V_A$ is the alveolar ventilation, and $V_M$ is the ratio of alveolar ventilation as the net effect of increase in the rate of metabolism to the resting value of ventilation and equals 0.988×(MRR-1), where MRR is the metabolic rate ratio (rate of metabolism divided by the basal rate of metabolism).

22. Method according to claim 21 wherein a predetermined value representing the patient's metabolic rate ratio is provided when the patient is at rest.

23. Method according to claim 21 wherein the data indicative of the patient's metabolic rate ratio is provided by a metabolic rate monitor when the patient is in exercise.

24. A method in accordance with claim 21 wherein the breathing frequency is determined according to the following relationship:

$$f=\frac{-K'V_D+\sqrt{(K'V_D)^2+4K'K''\pi^2V_{AR}V_D}}{2\pi^2V_DK''}$$

where f is the breathing frequency,
K' is the lung elastance,
K" is the air viscosity factor in the lungs,
$V_D$ is the dead space volume, and
$V_{AR}$ is the alveolar ventilation ($V_{AR}=V_A/60$).

25. A method in accordance with claim 16 further comprising the step of providing, based upon the values of the second pair of data signals, a first pulse for controlling the respirator, the first pulse having an amplitude corresponding to the level of required ventilation and having a duration which is only a fraction of the breathing period, this fraction representing an inspiratory time (%), providing a second pulse for controlling the valves in the output of the respirator, the second pulse having a constant amplitude and having a duration that is a major portion of the breathing cycle, and providing two additional pulse signals for controlling the respirator having characteristics representing total ventilation and the breathing frequency respectively.

26. Method according to claim 21 wherein the data representing metabolic rate ratio, lung elastance factor, air viscosity factor in the lung and barometric pressure is entered manually and stored in a software program.

27. Method according to claim 21 wherein the data representing metabolic rate ratio, lung elastance factor, air viscosity factor in the lung and barometric pressure is provided to the first means by monitors coupled to measure the same.

* * * * *

UNITED STATES PATENT AND TRADEMARK OFFICE
CERTIFICATE OF CORRECTION

PATENT NO. : 4,986,268

DATED : January 22, 1991

INVENTOR(S) : Fleur Taher Tehrani

It is certified that error appears in the above-identified patent and that said Letters Patent is hereby corrected as shown below:

Column 4, line 38, change "5" to --52--;

Column 5, line 3, change "$V_F$" to --$V'_F$--;

Column 5, line 18, change "$V_F$" to --$V'_F$--;

Column 5, line 36, change "$V_F$" to --$V'_F$--;

Column 6, line 28, change "$V_F$" to --$V'_F$--;

Column 6, line 44, change "$V_F$" to --$V'_F$--;

Column 6, line 67, change "$V_F$" to --$V'_F$--;

Column 7, line 67, change "20" TO --202--;

Column 9, line 58, change "v" to --v'--;

Column 9, line 60, change "K" to --K'--;

Column 10, line 6, change "W." to --W˙--;

Column 10, line 7, change "W. = Wf" to --W˙ = Wf--;

Column 10, line 10, change "W." to --W˙--;

Column 10, line 15, change "W." to --W˙--;

Column 10, line 20, change "W." to --W˙--;

UNITED STATES PATENT AND TRADEMARK OFFICE

CERTIFICATE OF CORRECTION

PATENT NO. : 4,986,268

DATED : January 22, 1991

INVENTOR(S) : Fleur Taher Tehrani

It is certified that error appears in the above-identified patent and that said Letters Patent is hereby corrected as shown below:

Column 13, claim 19, line 29, change "$P_{ao2}$" to --$P_{ao2}$--;

Column 13, claim 20, line 39, change "$(104XP_{ao2})^{4.9}$, to --$(104-P_{ao2})^{4.9}$--.

Signed and Sealed this

Twenty-eighth Day of July, 1992

*Attest:*

DOUGLAS B. COMER

*Attesting Officer*

*Acting Commissioner of Patents and Trademarks*